(12) United States Patent
Yiu

(10) Patent No.: US 8,551,117 B2
(45) Date of Patent: Oct. 8, 2013

(54) HANDHELD EXFOLIATING DEVICE

(75) Inventor: Wai Wah Yiu, Kowloon (HK)

(73) Assignee: Soft Lines International, Ltd., Kowloon (HK)

( * ) Notice: Subject to any disclaimer, the term of this patent is extended or adjusted under 35 U.S.C. 154(b) by 0 days.

(21) Appl. No.: 13/324,935

(22) Filed: Dec. 13, 2011

(65) Prior Publication Data
US 2012/0226289 A1 Sep. 6, 2012

Related U.S. Application Data

(60) Provisional application No. 61/449,567, filed on Mar. 4, 2011.

(51) Int. Cl.
A61B 17/50 (2006.01)

(52) U.S. Cl.
USPC .............................................. 606/131; 30/43.5

(58) Field of Classification Search
USPC ........................... 606/131, 133; 30/43.4, 43.5
See application file for complete search history.

(56) References Cited

U.S. PATENT DOCUMENTS

| | | | |
|---|---|---|---|
| 1,482,837 A | 2/1924 | Buck | |
| 2,395,296 A * | 2/1946 | Schwab | 30/41.6 |
| 2,867,214 A | 1/1959 | Wilson | |
| 5,377,699 A | 1/1995 | Varnum | |
| 5,918,607 A | 7/1999 | Zucker | |
| 6,055,731 A | 5/2000 | Zucker | |
| 6,305,084 B1 | 10/2001 | Zucker | |
| 6,391,034 B1 | 5/2002 | Adamson et al. | |
| 6,442,840 B2 | 9/2002 | Zucker | |
| 6,471,712 B2 * | 10/2002 | Burres | 606/131 |
| 6,523,546 B2 | 2/2003 | Jo et al. | |
| 6,551,262 B1 | 4/2003 | Lechtman | |
| 7,581,545 B1 | 9/2009 | Moldawski et al. | |
| 2007/0125097 A1 | 6/2007 | Habatjou | |

FOREIGN PATENT DOCUMENTS

| | | |
|---|---|---|
| CN | 101116576 | 2/2008 |
| CN | 201051937 | 4/2008 |
| DE | 201 04 304 | 5/2001 |
| DE | 201 04 304 U1 | 5/2001 |
| DE | 202008 05 686 | 7/2008 |
| JP | 2006-055489 | 3/2006 |
| KR | 10-2007-0017427 | 2/2007 |

OTHER PUBLICATIONS

International Search Report and Written Opinion for PCT Application PCT/IB2012/000474, mailed Jul. 12, 2012, 12 pages.
Images of a ROTOSHAVE razor believed to be on sale more than one year before the filing of the present application, 7 pages, 2010.

* cited by examiner

Primary Examiner — Victor Nguyen
(74) Attorney, Agent, or Firm — Foley & Lardner LLP

(57) ABSTRACT

A skin removal device includes a housing having a handle portion, a drum assembly coupled to the handle portion and including a drum, the drum having an abrasive outer surface configured to abrade skin of a user during rotation of the drum, and an electromechanical drive system disposed at least partially within the housing and configured to rotate the drum. The drum assembly is moveable in a lateral direction relative to the handle portion to enable insertion and removal of the drum assembly.

18 Claims, 5 Drawing Sheets

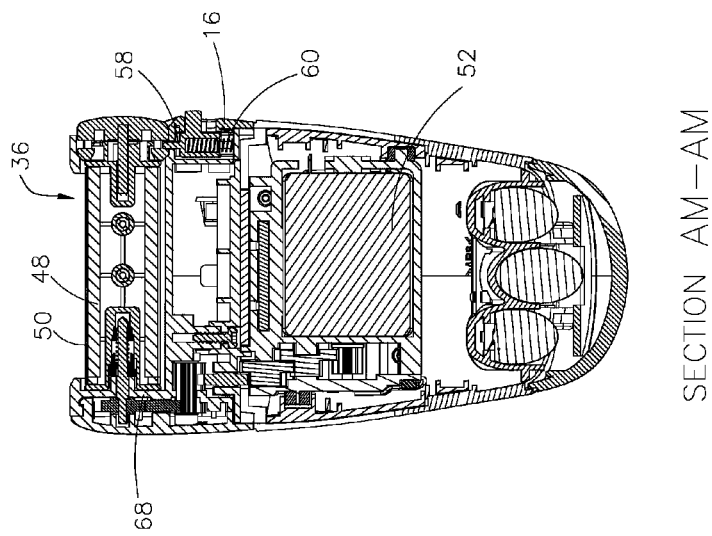
FIG.9 SECTION AM-AM
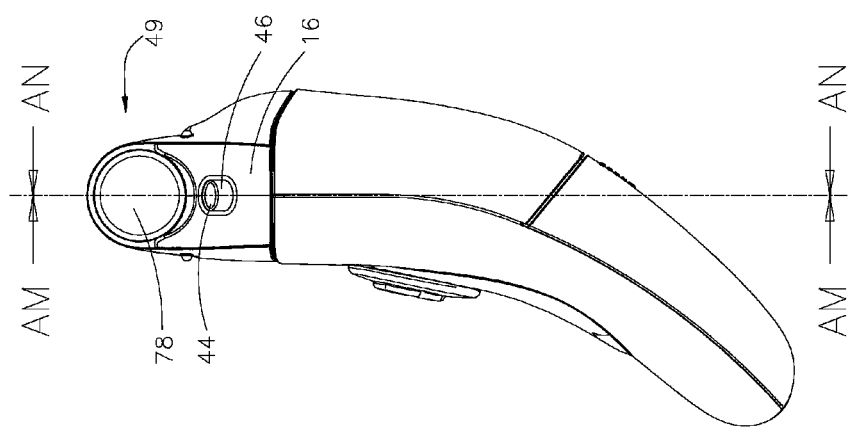
FIG.3
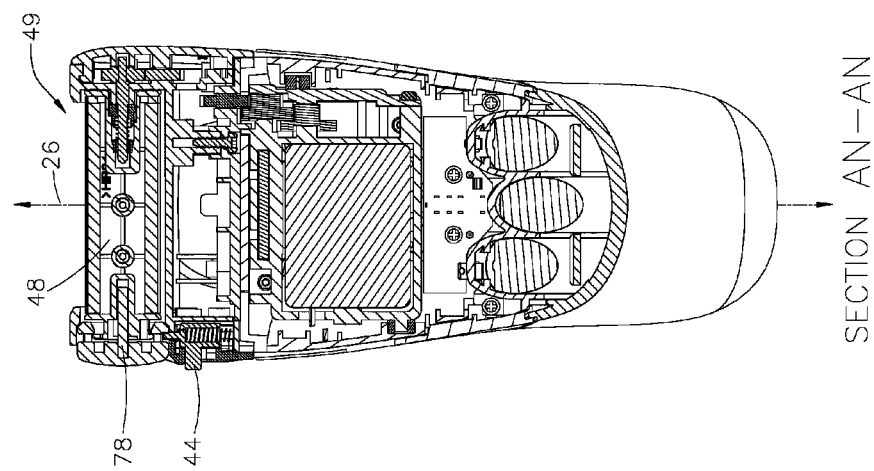
FIG.2 SECTION AN-AN

HANDHELD EXFOLIATING DEVICE

CROSS-REFERENCE TO RELATED PATENT APPLICATIONS

The present application claims the benefit of U.S. Provisional Application No. 61/449,567, filed Mar. 4, 2011, which is incorporated by reference herein in its entirety.

BACKGROUND

The present disclosure relates generally to the field of exfoliating devices. The present disclosure relates specifically to a handheld exfoliating device.

Outer layers of skin may be removed for a variety of reasons and in a variety of ways. Generally, exfoliation is the removal of dead skin cells from the skin's outer most layers and is part of many cosmetic techniques and procedures. Exfoliation can occur via mechanical removal of the skin, typically by rubbing the skin with an abrasive material. For example, during a pedicure, dead skin from the bottom of the feet may be removed using a pumice stone. Chemical exfoliant products containing various chemicals such as, salicylic acid, glycolic acid, fruit enzymes, citric acid, or malic acid, can also be used during exfoliation.

Various embodiments disclosed herein are directed to improved exfoliating devices and related methods.

SUMMARY

One embodiment relates to a skin removal device comprising a housing comprising a handle portion; a drum assembly coupled to the handle portion and comprising a drum having an abrasive outer surface configured to abrade skin of a user during rotation of the drum; and an electromechanical drive system disposed at least partially within the housing and configured to rotate the drum; wherein the drum assembly is moveable in a lateral direction relative to the handle portion to enable insertion and removal of the drum assembly.

Another embodiment relates to an exfoliating device comprising a housing comprising a handle portion and a mounting bracket extending from the handle portion; a drum assembly coupled to the handle portion and comprising a cylindrical drum having an abrasive outer surface configured to abrade skin of a user during rotation of the drum, the drum comprising an antimicrobial agent; a drive system disposed at least partially within the housing and configured to rotate the drum.

Another embodiment relates to a skin removal device comprising a handle portion; a mounting bracket coupled to the handle portion and having first and second lateral sides; and a drum assembly rotatably coupled to the mounting bracket, the drum assembly comprising a drum configured to rotate relative to the mounting bracket, the drum comprising an antimicrobial agent; wherein the drum assembly is insertable and removable in a lateral direction adjacent at least one of the lateral sides of the mounting bracket.

BRIEF DESCRIPTION OF THE DRAWINGS

This application will become more fully understood from the following detailed description, taken in conjunction with the accompanying figures, wherein like reference numerals refer to like elements.

FIG. 2 is a rear elevation view of the exfoliating device of FIG. 1 showing a cross-section of a portion of the motor head assembly taken along line AN-AN shown in FIG. 3.

FIG. 3 is a right side view of the exfoliating device of FIG. 1.

FIG. 9 is a cross-sectional view of a portion of the exfoliating device of FIG. 1 taken along line AM-AM in FIG. 3.

DETAILED DESCRIPTION

Before turning to the Figures, which illustrate the exemplary embodiments in detail, it should be understood that the present application is not limited to the details or methodology set forth in the description or illustrated in the Figures. It should also be understood that the terminology used herein is for the purpose of description and illustration only, and should not be regarded as limiting.

Figure 1:
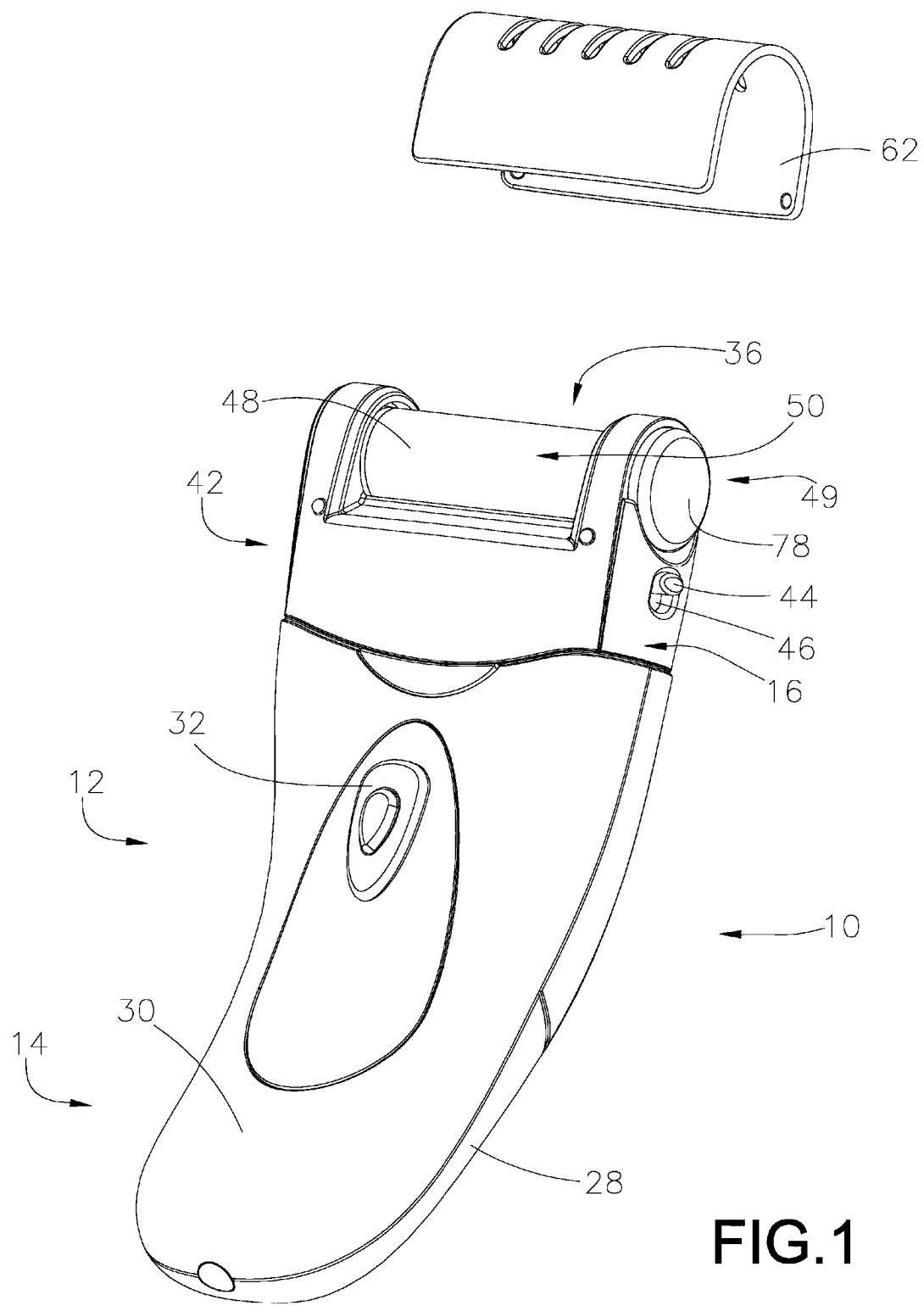
FIG. 1 is a perspective view of a handheld exfoliating device according to an exemplary embodiment.

Referring to FIG. 1, a skin removal device for removing outer, dead skin cells, shown as exfoliating device 10, is depicted according to an exemplary embodiment. Exfoliating device 10 may be configured for various cosmetic treatments or procedures involving skin removal. For example, exfoliating device 10 may be a pedicure device configured to remove skin from a person's foot. However, in other embodiments, exfoliating device 10 may be configured to remove skin from other parts of the body (e.g., hands, face, etc.). All such applications of device 10 are within the scope of the present disclosure. In the embodiments shown in FIGS. 1-9, exfoliating device 10 is a handheld, electric or automatic exfoliating device in which the exfoliating motion is supplied by an electro-mechanical drive mechanism (e.g., an electric motor, etc.). In other embodiments, exfoliating device 10 may be a manual, handheld exfoliating device in which the exfoliating action is provided manually. In yet another embodiment, exfoliating device 10 may be a combination manual, electric exfoliating device.

According to an exemplary embodiment, exfoliating device 10 includes a housing 12. Housing 12 generally supports and provides mounting for the various components of exfoliating device 10. In one embodiment, housing 12 defines a handle portion 14 and a head mounting bracket 16. Handle portion 14 is shaped to provide a comfortable gripping structure to allow a user to hold and to manipulate exfoliating device 10 during use. Handle portion 14 includes a pair of opposite lateral sides that may include various griping features to facilitate grasping of handle portion 14 (e.g., a raised, textured surface that also facilitates gripping, a compliant rubber-type material that facilitates griping while the rest of handle 14 is formed of a rigid material the provides the overall shape and rigidity to handle 14, etc.). Lateral gripping sections may make holding handle 14 easier due to the increased friction between the user's hand and the compliant material of the lateral grip sections.

In one embodiment, as shown in FIG. 2, handle 14 is shaped such that the lateral surfaces of handle portion 14 are concave and curve inwardly toward the central portion of handle 14. Thus, in this embodiment, handle 14 includes a reduced diameter portion spaced below head mounting bracket 16. Located at the lower end of handle 14 is a battery door 28 that provides access to batteries that provide power to exfoliating device 10.

Referring to FIG. 1, handle 14 of exfoliating device 10 includes a front surface 30, and an activation switch 32 is positioned along front surface 30. Activation switch 32 may be toggled between on and off positions, allowing the user to activate and deactivate exfoliating device 10. Activation switch 32 is positioned along front surface 30 between the lateral sides of handle portion 14 such that the user may access activation switch 32 with the user's fingers or thumb while handle portion 14 is grasped within the user's hand. In one embodiment, activation switch 32 may be positioned within a recess (not shown) formed in front surface 30 of handle 14 such that the outer face or surface of activation switch 32 is recessed below front surface 30 of handle 14, which may make inadvertent actuation of activation switch 32 less likely.

Referring to FIG. 1, mounting bracket 16 extends from an upper end or portion of handle 14. Mounting bracket 16 is coupled to and supports a motor head assembly 36. As best seen in FIG. 3, in one embodiment mounting bracket 16 is a generally straight mounting bracket generally aligned with the upper portion of handle portion 14. In other embodiments, mounting bracket 16 may be a curved or bent member and include a lower section and an upper section positioned at an angle relative to the lower section (e.g., at an angle between about zero degrees and 90 degrees, specifically between about 15 degrees and 45 degrees, and more specifically between about 25 degrees and 35 degrees). The shape and size of mounting bracket 16 may be selected to facilitate the positioning of the exfoliating portion of motor head assembly 36 against the user's skin during exfoliation.

Referring further to FIG. 1, in one embodiment motor head assembly 36 is coupled to and rigidly supported by mounting bracket 16 such that a user grasping handle 14 is able to manipulate and position motor head assembly 36 during use. Motor head assembly 36 includes a housing 42 that generally provides support for the components of motor head assembly 36. Motor head assembly 36 also includes a mounting post 44 extending from one of the lateral sides of motor head assembly 36. Mounting bracket 16 includes an aperture 46 that receives mounting post 44. Aperture 46 facilitates location of motor head assembly 36 relative to mounting bracket 16 during assembly and also provides engagement that substantially fixes motor head assembly 36 in place relative to mounting bracket 16.

Referring to FIGS. 1-3, motor head assembly 36 includes an exfoliating head or drum assembly 49. Exfoliating head assembly 49 includes an exfoliating head, shown as drum 48, and an end hub 78 coupled to one of the lateral ends of drum 48. Drum 48 is the rotating element of exfoliating head assembly 49 and is rotatably coupled to end hub 78. In the embodiment shown, drum 48 is a cylindrical structure that is rotatably mounted such that drum 48 is allowed to rotate relative to housing 42 of motor head assembly 36. When motor head assembly 36 is coupled to mounting bracket 16 as shown in FIG. 1, at least a portion of drum 48 is positioned above the upper end of mounting bracket 16 and located at the upper end of exfoliating device 10. Drum 48 includes an outer surface 50 configured to remove or abrade (e.g., grind, pulverize, etc.) skin, providing the exfoliating functionality of exfoliating device 10. In one embodiment, head assembly 49 and/or drum 48 are configured to be inserted and/or removed in a lateral direction, permitting the drum or its outer surface to be cleaned, maintained, replaced, etc.

In one embodiment, abrasive outer surface 50 may be or include a coating and may be formed by embedding or affixing a gritty material, such as pumice, directly to the outer surface of drum 48. In another embodiment, a sheet of abrasive material (e.g., a sandpaper material) may be adhered to drum 48 to form outer surface 50. In another embodiment, exfoliating device 10 may include a plurality of drums 48 each having different abrasive outer surfaces 50 providing different levels of coarseness or abrasiveness. In this embodiment, the user may select and install a drum 48 depending on the user's desire or need for a particular use. Further, as explained in more detail below, motor head assembly 36 may be configured to allow the user to easily switch or replace drum 48 of motor head assembly 36.

According to various exemplary embodiments, outer surface 50 may include an anti-microbial and/or anti-bacterial substance or agent 51 (e.g., a compound, a powder, etc.) configured to inhibit the growth of undesirable microorganisms such as bacteria, fungi, etc. Agent 51 may be provided as a part of the coating formed on outer surface 50 of drum 48. For example, in some embodiments, agent 51 may be mixed with an abrasive material and the mixture subsequently coated or otherwise applied to drum 48. According to one embodiment, agent 51 makes up between approximately 1-12 percent of the coating of outer surface 50, while in other embodiments relatively more or less of agent 51 may be utilized. In yet further embodiments, agent 51 may be applied to the surface of the coating (e.g., sprayed, brushed, sifted, etc.) or integrated into the coating on drum 48 using any of a variety of other alternative methods (e.g. adhesives, etc).

According to one embodiment, agent 51 is a powder (e.g., a solid). According to other embodiments, other types of agents may be used, including liquids, semi-solids, pastes, etc. The type and/or amount of agent utilized may be varied based on the intended usage of the exfoliating device (e.g., based on what part of the body the device is intended to be used, etc.) and/or other factors.

As shown in FIG. 1, exfoliating device 10 may also include a cover 62 that is configured to be coupled to mounting bracket 16 to partially encloses portion of motor head assembly 36. Cover 62 provides protection to drum 48 and covers outer surface 50 of drum 48. In this manner, cover 62 limits inadvertent contact with drum 48 when exfoliating device 10 is not in use. Cover 62 may be secured to mounting bracket 16 via a press-fit engagement or other suitable coupling (e.g., snap-fit, friction fit, indents/detents, etc.).

Figure 6:
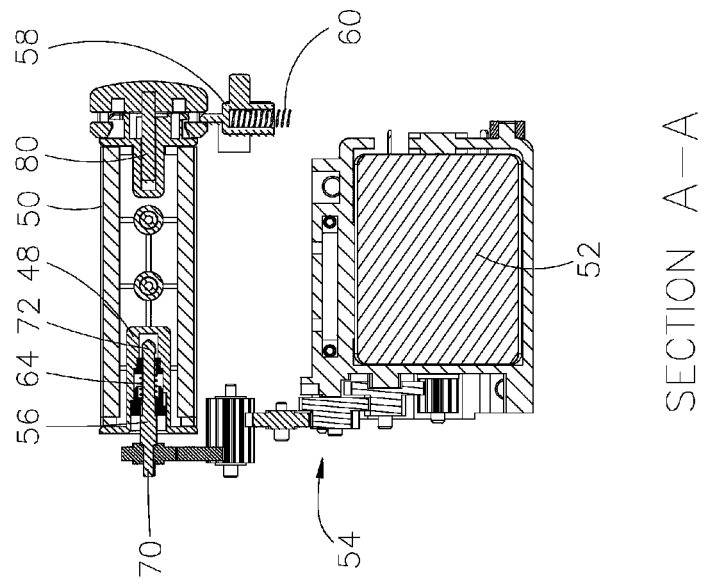
FIG. 6 is a sectional view of the motor head assembly of FIG. 4 taken along line A-A shown in FIG. 5.
Figure 5:
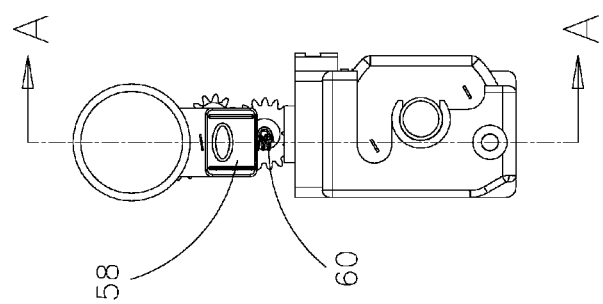
FIG. 5 is a right side view of the motor head assembly of FIG. 4.
Figure 4:
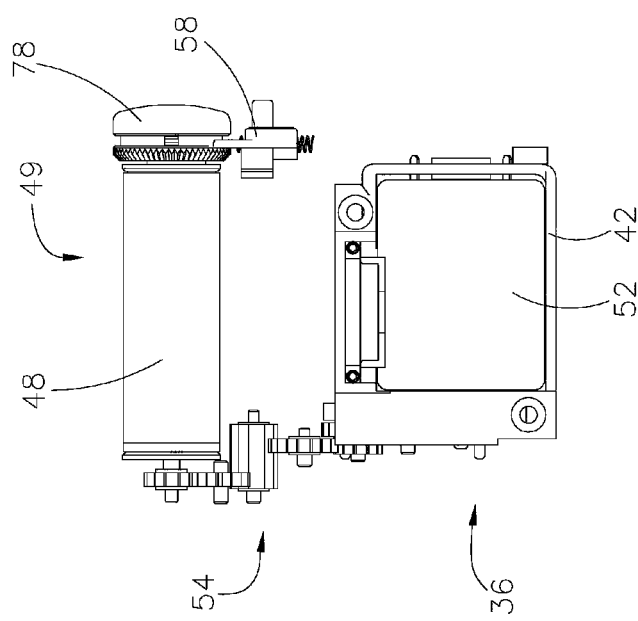
FIG. 4 is a front view of a motor head assembly for use with an exfoliating device according to an exemplary embodiment.

Referring to FIGS. 4-6, motor head assembly 36 is shown disconnected from mounting bracket 16. According to an exemplary embodiment, an electro-mechanical drive system is utilized to rotate drum 48. For example, in one embodiment motor head assembly 36 may include an electric motor 52, a series of gears 54, and a drive shaft 56. Drum 48 includes a cavity 64 defined within the body of drum 48, and drive shaft 56 includes a first end 70 and a second end 72. Drive shaft 56 is received within cavity 64 of drum 48, and second end 72 is the free end of drive shaft 56 that is located within cavity 64. Gears 54 are coupled to an output shaft of electric motor 52 and to first end 70 of drive shaft 56. Gears 54 transmit rotational motion from electric motor 52 to drive shaft 56. Drum 48 is rigidly coupled to drive shaft 56 such that rotation of drive shaft 56 causes a corresponding rotation of drum 48.

In use, upon a user activating device 10 (e.g., buy activation of witch 32), motor 52 causes drum 48 to rotate, and the user places the abrasive outer surface 50 of drum 48 in contact with skin that the user wishes to remove. As drum 48 rotates, outer surface 50 of drum 48 rubs or abrades the outer layer of the user's skin resulting in removal of dead skin cells.

Figure 8:
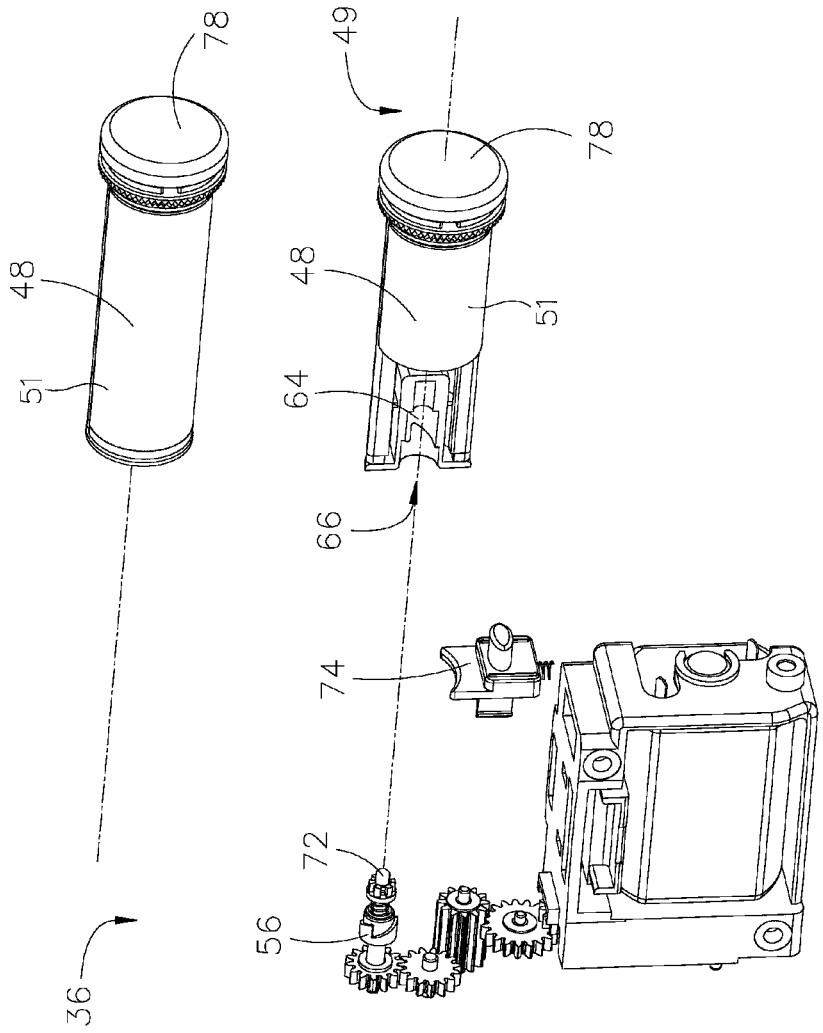
FIG. 8 is an exploded view of the motor head assembly of FIG. 7 showing a partial cut-away view of a exfoliating head, according to an exemplary embodiment.
Figure 7:
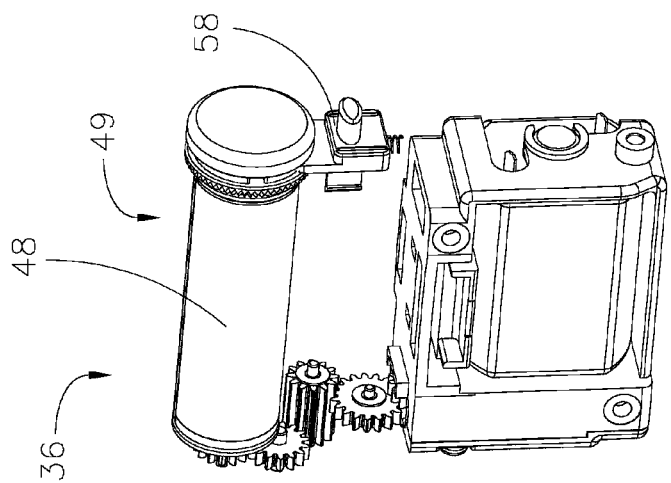
FIG. 7 is a perspective view of the motor head assembly of FIG. 4 shown following assembly.

As shown in FIGS. 4, 6 and 8, motor head assembly 36 includes a support bracket 58. Exfoliating head assembly 49 is supported by support bracket 58 and drive shaft 56. In particular, as shown in FIG. 8, drive shaft 56 supports one end of exfoliating head assembly 49 via the coupling between drum 48 and drive shaft 56. The other end of exfoliating head assembly 49 is supported via contact between end hub 78 and support bracket 58. As shown in FIG. 8, support bracket 58 includes an arcuate upper surface 74 shaped to match the curve of an outer surface of end hub 78 providing a support surface that partially surrounds a portion of end hub 78.

As noted above, the engagement between drive shaft 56 and drum 48 forms a rigid connection such that rotation of drive shaft 56 causes a corresponding rotation of drum 48. As shown in FIG. 8, cavity 64 of drum 48 forms an opening 66 through one of the lateral faces of drum 48, and cavity 64 extends at least part of the way through drum 48. End 72 of drive shaft 56 is sized to form a press-fit or friction fit engagement within cavity 64 of drum 48. In another embodiment, end 72 of drive shaft 56 includes one or more projecting elements configured to engage cooperating recesses within cavity 64 to ensure transfer of rotational motion of drive shaft 56 to drum 48. In one such embodiment, end 72 may be sized to form a snap-fit engagement within cavity 64.

As shown in FIGS. 6 and 8, the end of drum 48 opposite opening 66 is coupled to end hub 78 via a shaft 80. Shaft 80 is rigidly connected to end hub 78, and drum 48 is rotatably connected to shaft 80. Thus, as drum 48 is rotated by drive shaft 56, drum 48 rotates relative to shaft 80 and end hub 78. In another embodiment, shaft 80 is rotatably coupled to end hub 78 and is rigidly connected to drum 48. Thus, in this embodiment, as drum 48 is rotated by drive shaft 56, both drum 48 and shaft 80 rotate together relative to end hub 78.

To allow drum 48 to rotate, a second support bracket 68 (see FIG. 9) is configured such that drum 48 is permitted to rotate relative to the second support bracket 68. Second support bracket 68 is configured to rotatably support drive shaft 56 and facilitate rotation of drum 48 relative to second support bracket 68. In one embodiment, second support bracket 68 is shaped to be slightly larger than the diameter of drum 48. In a further embodiment, second support bracket 68 may include a recess (not shown) to provide a rotational bearing surface allowing drum 48 to spin or rotate freely within the recess.

In one embodiment, drive shaft 56 is permanently coupled to gears 54, and exfoliating head assembly 49, and specifically drum 48, is removably coupled (i.e., not permanently coupled to) to drive shaft 56. This configuration allows exfoliating head assembly 49 to be removed and replaced while drive shaft 56 remains in place coupled to gears 54. This allows the user to switch between drums having different abrasion properties by exchanging the exfoliating head assembly 49 currently coupled to motor head assembly 36. This configuration also allows for the replacement an old drum 48 with an exfoliating head assembly 49 having new drum 48 without requiring drive shaft 56 to be decoupled from motor head assembly 36. Because drive shaft 56 remains coupled to gears 54 after exfoliating head assembly 49 has been removed (as shown in FIG. 8), drive shaft 56 may act as a locating feature helping the user to align the new exfoliating head assembly 49 during assembly to ensure it is properly installed relative to motor head assembly 36. Further, exfoliating head assembly 49 may be easier to manufacture and less expensive than a head assembly having a permanently attached drive shaft.

Referring to FIG. 9, a cross-section of motor head assembly 36 is shown coupled to mounting bracket 16. As shown in FIG. 9, a spring 60 is coupled to the lower end of support bracket 58, and when motor head assembly 36 is coupled to mounting bracket 16, a spring 60 is engaged between support bracket 58 and an inner surface of mounting bracket 16. In this manner, spring 60 biases drum 48 upward to assist in maintaining contact between outer surface 50 of drum 48 and the user's skin during use.

Figure 10:
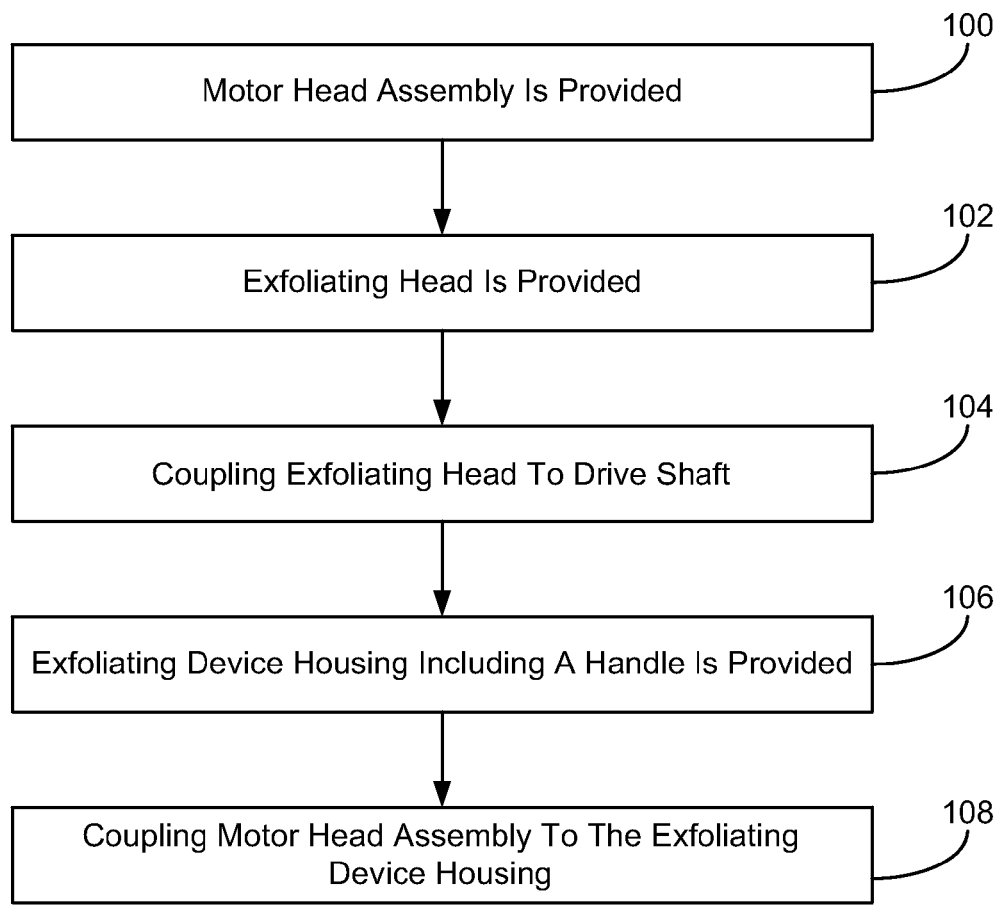
FIG. 10 is flow diagram showing assembly of an exfoliating device, according to an exemplary embodiment.

Referring to FIG. 10 a method of assembling an exfoliating device is shown according to an exemplary embodiment. At step 100, a motor head assembly is provided. The motor head assembly includes a housing and a drive shaft supported by the housing. The drive shaft is coupled to a motor via gears such that the motor causes rotation of the drive shaft. In one embodiment, the motor head assembly may be motor head assembly 36 discussed above. At step 102, an exfoliating head is provided. The exfoliating head may be a cylindrical drum including a central cavity having an opening formed in one of the lateral sides of the drum. In one embodiment, the exfoliating head may be drum 48 discussed above and may include an anti-microbial agent or compound.

At step 104, the exfoliating head is coupled to a drive shaft of the motor head assembly. In one embodiment, the opening in the lateral side of the exfoliation head is aligned with the drive shaft, and the exfoliating head is mounted to the drive shaft by moving the head laterally such that the drive shaft is received within the cavity of the head. In one embodiment, the exfoliating head is coupled to the drive shaft via a press-fit or friction-fit between the outer surface of the drive shaft and the inner surface of the head cavity. In another embodiment, the exfoliating head is coupled to the drive shaft via a snap-fit engagement. At step 106, an exfoliating device housing including a handle is provided, and at step 108, the motor head assembly is coupled to the exfoliating device housing. In one embodiment, the motor head assembly is coupled to the exfoliating device housing after the exfoliating head is coupled to the motor head assembly. In another embodiment, the exfoliating drum may be coupled to the drive shaft when the motor head assembly is coupled to the exfoliating device housing.

Some embodiments herein relate to a skin removal device for removing dead skin cells from the outer layer of skin of a user. The device includes a motor, a drive shaft, and a drum coupled to the drive shaft such that rotational motion generated by the motor is transferred to the drum. The outer surface of the drum is configured to abrade the skin of the user during rotation. The drum includes a cavity extending from one lateral end of the drum along at least a portion of the length of the drum, and the drive shaft is received within the cavity to couple the drum to the drive shaft.

In some embodiments, a method of assembling an exfoliating device includes providing an exfoliating device housing having a handle. In one embodiment, the method includes coupling a motor head assembly to the exfoliating device housing after the exfoliating head is coupled to the drive shaft. In another embodiment, the exfoliating drum may be coupled to the drive shaft when the motor head assembly is coupled to the exfoliating device housing. In one embodiment, an opening in the lateral side of the exfoliating head is aligned with the drive shaft, and the exfoliating head is mounted to the drive shaft by moving the head laterally such that the drive shaft is received within the cavity of the head. In one embodiment, the exfoliating head is coupled to the drive shaft via a press-fit or friction-fit between the outer surface of the drive shaft and the inner surface of the cavity. In another embodiment, the exfoliating head is coupled to the drive shaft via a snap-fit engagement. Various exemplary embodiments relate to the method of assembling an exfoliating device, as recited above, and including any combination of one or more features recited in the detailed description and shown in the figures.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A skin removal device comprising:
   a housing comprising a handle portion;
   a drum assembly removably coupled to the handle portion and comprising:
       a drum having an abrasive outer surface configured to abrade skin of a user during rotation of the drum;
       a recess formed in a first end of the drum;
       a hub coupled to a second end of the drum, the hub comprising an annular groove; and
   an electromechanical drive system disposed at least partially within the housing and configured to rotate the drum, the electromechanical drive system comprising:
       a drive shaft, at least a portion of which is received in the recess of the drum to rotatably fix the drive shaft relative to the drum such that the drum rotates with the drive shaft about an axis of the drive shaft; and
       an electric motor coupled to the drum assembly via a plurality of gears and the drive shaft;
   a mounting bracket extending from the housing and configured to support the drum assembly, the mounting bracket comprising at least one U-shaped support bracket configured to rotatably support the hub of the drum assembly, wherein the support bracket engages the annular groove to rotatably maintain a position of the drum assembly relative to the mounting bracket;
   wherein the drum assembly is movable in a lateral direction relative to the handle portion to enable insertion and removal of the drum assembly; and wherein when the drum assembly is removed from the housing, the drive shaft remains coupled to the housing.

2. The device of claim 1, wherein an outer surface of the drum comprises an antimicrobial agent.

3. The device of claim 1, wherein the outer surface of the drum comprises an abrasive sheet of material.

4. The device of claim 1, wherein the drive shaft is configured to engage the recess in a friction fit manner.

5. The device of claim 1, further comprising
   a biasing member configured to provide a biasing force between the mounting bracket and the drum assembly to bias the drum toward the skin of the user during use of the device.

6. An exfoliating device comprising:
   a housing comprising a handle portion and a mounting bracket extending from the handle portion;
   a drum assembly removably coupled to the handle portion and comprising:
       a cylindrical drum having an abrasive outer surface configured to abrade skin of a user during rotation of the drum;
       a cavity formed in a first end of the drum; and
       an end hub coupled to a second end of the drum, the end hub comprising an annular groove;
   a drive system disposed at least partially within the housing and configured to rotate the drum via a drive shaft received in the cavity of the drum assembly; the drive shaft being coaxial with a longitudinal axis of the drum such that during operation the drum rotates about the drive shaft, the drive system comprising an electric motor interconnected with the drive shaft via a plurality of spur gears;
   a support bracket movably coupled to the mounting bracket, the support bracket comprising an arcuate surface to support the end hub of the drum assembly, wherein the support bracket engages the annular groove to rotatably maintain a position of the drum assembly relative to the mounting bracket;
   wherein when the drum assembly is removed from the exfoliating device, the drive shaft remains coupled to the drive system.

7. The device of claim 6, wherein the drum assembly is insertable into and removable from the housing via a lateral side of the handle portion.

8. The device of claim 6,
   wherein the drive shaft is received within the recess to rotationally fix the drum relative to the drive shaft.

9. The device of claim 6, further comprising a spring member configured to bias the drum relative to the mounting bracket and toward the skin of the user.

10. The device of claim 6, further comprising a cover configured to engage the handle portion in a snap-fit fashion and substantially cover the drum assembly.

11. The device of claim 6, further comprising a coating on an outer surface of the drum, the coating comprising an antimicrobial agent making up between 1 and 12 percent of the coating.

12. The device of claim 6, wherein when the drum is inserted into the skin removal device, the drive shaft acts as a locating feature to align the drum relative to the skin removal device.

13. The device of claim 6, further comprising a spring providing a spring force biasing the support bracket toward the drum assembly.

14. The device of claim 13, wherein when the support bracket is moved against the spring force, the support bracket disengages from the end hub and allows the drum assembly to be removed from the skin removal device.

15. The device of claim 14, wherein the support bracket comprises a post configured to extend at least partially through an aperture in one of the lateral sides of the mounting bracket, the post configured to facilitate movement of the support bracket.

16. A skin removal device, comprising:
    a housing comprising a handle portion;

a mounting bracket coupled to the handle portion, having first and second lateral sides, and comprising a U-shaped support;

a drum assembly removably coupled to the mounting bracket, the drum assembly comprising:

a drum configured to rotate relative to the mounting bracket, the drum comprising an antimicrobial agent; and an end hub coupled to a first end of the drum assembly and defining an annular groove, the annular groove engaged by the support of the mounting bracket to at least partially maintain a position of the drum assembly relative to the mounting bracket; and a drive system configured to rotate the drum about an axis of a drive shaft received in a recess formed in a second end of the drum assembly, the drive system comprising a motor and a plurality of gears operably coupling the motor and the drive shaft;

wherein the drum assembly is insertable and removable in a lateral direction adjacent at least one of the lateral sides of the mounting bracket and wherein when the drum assembly is removed from the skin removal device, the drive shaft remains coupled to the device.

17. The device of claim 16, further comprising a spring configured to bias the drum toward the skin of a user during use.

18. The device of claim 16, wherein the drum assembly comprises a projection configured to extend at least partially through an aperture in one of the lateral sides of the mounting bracket, the projection configured to at least partially maintain the position of the drum assembly relative to the mounting bracket.

* * * * *